(12) United States Patent
Stejskal et al.

(10) Patent No.: US 9,101,702 B2
(45) Date of Patent: Aug. 11, 2015

(54) FLEXIBLE TUBING PUMP AND THEREWITH EQUIPPED BLOOD TREATMENT DEVICE

(75) Inventors: Martin Stejskal, Bad Soden (DE); Wolfram Langkau, Steinbach (DE); Stefan Oesterreich, Neu-Anspach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 331 days.

(21) Appl. No.: 13/360,313

(22) Filed: Jan. 27, 2012

(65) Prior Publication Data
US 2012/0195777 A1 Aug. 2, 2012

Related U.S. Application Data

(60) Provisional application No. 61/437,025, filed on Jan. 28, 2011.

(30) Foreign Application Priority Data

Jan. 28, 2011 (DE) .......................... 10 2011 009 777

(51) Int. Cl.
*F04B 43/12* (2006.01)
*A61M 1/10* (2006.01)

(52) U.S. Cl.
CPC ........... *A61M 1/1037* (2013.01); *A61M 1/1039* (2014.02); *F04B 43/1253* (2013.01); *F04B 43/1261* (2013.01)

(58) Field of Classification Search
CPC ........... F04B 43/1253; F04B 43/1261; A61M 1/1039
USPC ...................... 417/476, 477.1, 477.9; 604/153
See application file for complete search history.

(56) References Cited

U.S. PATENT DOCUMENTS

| | | | | |
|---|---|---|---|---|
| 4,472,116 | A | * | 9/1984 | Wenstrup .................... 417/477.2 |
| 5,230,614 | A | * | 7/1993 | Zanger et al. .............. 417/477.9 |
| 5,256,041 | A | * | 10/1993 | Tucker ........................ 417/477.9 |
| 6,099,272 | A | * | 8/2000 | Armstrong et al. ........... 417/476 |

(Continued)

FOREIGN PATENT DOCUMENTS

| | | |
|---|---|---|
| DE | 2918797 A1 | 11/1980 |
| DE | 44 47 801 B4 | 2/2009 |

(Continued)

OTHER PUBLICATIONS

PCT International Search Report from PCT/EP2012/000369, mailed on May 18, 2012.

*Primary Examiner* — Charles Freay
(74) *Attorney, Agent, or Firm* — Kenyon & Kenyon LLP (57) ABSTRACT

The invention describes a tubing pump for accommodation of at least one section of a flexible tubing with at least one stator and at least one rotor that pivots around an axis of rotation in the stator, in which the stator surrounds or completely or partially confines the rotor, sparing out/with a first opening intended for inserting of the flexible tubing into the pump, and a separate second opening to lead the flexible tubing out of the pump sparing out/and with a section arranged between the first opening and the second opening of the tubing pump and/or the stator comprising an edge or a section at the place of the second opening to lead the tubing, which is nearer to the axis of rotation of the rotor than all other sections of the stator. The invention further describes a blood treatment device including the blood pump.

18 Claims, 6 Drawing Sheets

(56) References Cited

U.S. PATENT DOCUMENTS

| | | | |
|---|---|---|---|
| 6,948,638 B2 * | 9/2005 | Tu | 222/209 |
| 2004/0037724 A1 * | 2/2004 | Haser et al. | 417/477.9 |
| 2004/0131487 A1 * | 7/2004 | Ito | 417/476 |
| 2006/0177328 A1 | 8/2006 | Nordell et al. | |
| 2007/0296744 A1 * | 12/2007 | Kubota et al. | 347/7 |
| 2008/0095645 A1 * | 4/2008 | Tam | 417/410.3 |
| 2010/0129248 A1 * | 5/2010 | Mou | 417/477.9 |
| 2010/0202907 A1 | 8/2010 | Klein | |

FOREIGN PATENT DOCUMENTS

| | | |
|---|---|---|
| EP | 0019205 | 11/1980 |
| EP | 1 469 201 A2 | 10/2004 |
| EP | 1 767 232 A1 | 3/2007 |
| GB | 2284576 | 6/1995 |
| WO | 2009/025686 A1 | 2/2009 |

\* cited by examiner

FLEXIBLE TUBING PUMP AND THEREWITH EQUIPPED BLOOD TREATMENT DEVICE

CROSS REFERENCE TO RELATED APPLICATIONS

This application claims priority to U.S. Provisional Application Ser. No. 61/437,025 filed Jan. 28, 2011 and German Patent Application No. 10 2011 009 777.5 filed Jan. 28, 2011.

FIELD OF INVENTION

The present invention describes a flexible tubing pump. It further describes a blood treatment device.

BACKGROUND OF THE INVENTION

Flexible tubing pumps are known in medical practice. In pumps of this kind a flexible tube or tubing (which terms are synonymously used herein) is inserted in which a medical liquid fluid is contained, e.g. blood in extracorporeal circulation during a blood treatment such as hemodialysis. By means of the above-mentioned pump, the fluid in the flexible tubing is conveyed within the flexible tubing.

SUMMARY OF THE INVENTION

One aim of the present invention is to suggest a further flexible tubing pump of the above-mentioned kind. The object according to the present invention is accomplished by a flexible tubing pump.

According to the present invention the flexible tubing pump (in the following abbreviated to: pump or pump according to the present invention) serves as a receptacle for at least one section of the flexible tubing. The pump contains at least one stator and at least one rotor in the stator which pivots around an axis of rotation.

The stator surrounds or completely or partially confines the rotor, with a first opening intended for insertion of the flexible tubing into the pump, and a second opening intended to lead the flexible tubing out of the pump. The first and the second openings are positioned separately from each other.

Between the first and the second opening is a section which is assigned to the stator or another section of the pump. This section has an edge (or protrusion) or an area at the place where the second opening for the exit of the tubing is positioned, which is nearer to the axis of rotation of the rotor than some or all other sections of the stator.

The aim according to the present invention is achieved by a blood treatment device, which consists of at least one tubing pump according to the present invention.

Embodiments according to the present invention can have one or several features described as follows.

In all of the following embodiments the term can be or can have etc. is used as a synonym for is preferably or has preferably in order to illustrate certain embodiments according to the present invention.

The distance between the at least one section and the axis of rotation of the rotor is or are each determined in certain embodiments according to the present invention perpendicular to the axis of rotation, as in the distances of the remaining sections. The term axis of rotation describes the geometrical position of an infinite straight line.

In some embodiments according to the present invention the edge extends into the direction towards the rotor, and/or towards the axis of rotation, and/or radially inwards, and/or towards the inside of the blood pump.

In some embodiments according to the present invention the stator and/or the area between the first and the second opening surrounds or confines the rotor in a level perpendicular to the axis of rotation or in a level of rotation of the rotor and/or in a level parallel to the level of rotation.

The number of recesses is preferably at least two. It may alternatively be higher, i.e. three or four or more recesses can be intended. The recesses can furthermore be at positions where no tubing enters or exits the space between stator and rotor.

In certain embodiments according to the present invention all recesses are separated by stator material or material which is joined in one piece with the stator. In other embodiments according to the present invention all recesses are separated from each other by the material of the pump according to the present invention which is not part of the stator. In certain embodiments according to the present invention the recesses are separated by material of the stator as well as by material which is not part of the stator.

In some embodiments according to the present invention the first opening is positioned upstream in relation to the second opening regarding the direction of flow of the fluid flowing inside the tube during regular use of the pump. In other words, the fluid flowing in the tube reaches the first opening before reaching the second opening.

In certain embodiments according to the present invention the pump is a peristaltic pump and/or a roller pump.

In some embodiments according to the present invention the pump is intended to convey an anticoagulation solution, in particular to convey citrate- and calcium solutions and furthermore heparin solutions. In some embodiments according to the present invention the pump is intended to be a flexible tubing pump for blood. In certain embodiments according to the present invention the pump is intended to convey dialysate, filtrate substitute or similar. The pump according to the present invention and/or the blood treatment device according to the present invention each can show a switching mechanism for control and regulation according to the use.

In some embodiments according to the present invention the pump does not have a detachable cover element for prevention of entangling or injury at the points of entrance or exit where tube enters or exits the pump.

In some embodiments according to the present invention the pump does not have a cover element for prevention of entangling or injury at the points of entrance or exit where tube enters or exits the pump which is not joined in one piece with the stator and/or the housing of the pump.

In certain embodiments according to the present invention a protection from entangling or injury is achieved solely by the design and/or concurrence of the rotor and/or the stator and the components thereof.

In some embodiments according to the present invention the areas of the stator that surround the rotor jut out of the rotor in a direction along the axis of rotation, or cover the rotor, or are flush with the rotor (especially flush in one direction out of the pump).

In some embodiments according to the present invention merely a rotor cover which optionally contains additional rotor handles is not covered. In these few embodiments according to the present invention all other components of the rotor are covered by the stator.

In certain embodiments according to the present invention the areas of the stator surrounding the rotor are at least the areas of the stator which come into contact with the tube or serve as a counter bearing for the tube during use of the pump. In some embodiments according to the present invention the area described is the one which shows a smaller distance to the axis of rotation of the rotor and/or the area which is between both openings for the tube.

In certain embodiments according to the present invention the areas of the stator which surround the rotor cover at least the rotating areas of the rotor during use or advantageously cover these against e.g. contact.

In some embodiments according to the present invention the area or edge with the lesser distance to the axis of rotation is designed to neither touch areas of the rotor nor be in contact with other parts of the stator apart from the area between the first and the second opening.

In certain embodiments according to the present invention the area between the first and the second opening protrudes nose-like or is shaped like a nose.

In certain embodiments of the pump according to the present invention the first and/or the second opening are open to the front looking at the pump from the front. A cover that would prevent the view of the tube being led through the first and/or the second opening during use of the pump is not provided for in these embodiments. This advantageously allows a convenient insertion and removal of the tube into or out of the pump. It can also advantageously contribute to keeping costs of production and assembly of the pump low.

In some embodiments according to the present invention the area or edge with the lesser distance to the axis of rotation is designed in an area between the separate openings and which is not in the way of fluid movement or moving devices (e.g. rollers) of the rotor.

In certain embodiments according to the present invention the area or edge or protrusion which is nearer to the axis of rotation does not redirect the tube towards a desired direction.

In some embodiments of the pump according to the present invention the inserted tubing does not touch the area or edge (also referred to herein as a protrusion).

In certain embodiments according to the present invention the area or edge or protrusion which is nearer to the axis of rotation is not in the raceway or way of the displacers, fluid movement devices, or rollers of the pump according to the present invention or the pump's rotor.

In certain embodiments according to the present invention the term not in the way of fluid moving devices means that the area or edge with the lesser distance to the axis of rotation is not in contact with a raceway or running surface of or at the stator and/or with the tube during standard operation. This conveniently allows the dimensions of the pump to be minimized, at least regarding an installation depth or extension in the direction of the axis of rotation. In this embodiment the pump advantageously only slightly protrudes for example from the front section of the blood treatment device according to the present invention.

In some embodiments according to the present invention the fluid movement devices are rollers.

In certain embodiments according to the present invention the area or edge with the lesser distance to the axis of rotation in a level perpendicular to the axis of rotation becomes narrower towards the end or the tip of that area in a direction conversely to the intended direction of the rotor.

The end of the area or edge may be the end which is nearer to the direction of rotation of the rotor during standard operation.

In some embodiments according to the present invention the area with the lesser distance to the axis of rotation is more pointed towards its end (i.e. the angle by which the outer contours run towards each other becomes smaller). In some embodiments according to the present invention this area is wedge-shaped, where the tip of the wedge points conversely to the direction of rotation of the rotor.

In some embodiments according to the present invention the tip, the pointed end or the wedge-shaped end can be found in a sectional plane through the area with the lesser distance to the axis of rotation in a level perpendicular to the axis of rotation.

In some embodiments according to the present invention the rotor features a rotor cover which rotates simultaneously with the rotor during use of the pump. The rotor cover may feature a gripping section with or without winged grips. In these embodiments the area or edge which is nearer to the axis of rotation of the rotor is arranged in relation to the pump in such a way that a gap which is in a radial direction between the rotating rotor cover and the area or edge which is nearer does not exceed a pre-determined width.

In some embodiments according to the present invention the pre-determined width is any desired width which is smaller than all the widths of the gaps between the rotor cover (or an edge hereof) and other sections surrounding the rotor. In a level perpendicular to the axis of rotation it could, e.g., be ascertained if this criteria is fulfilled, preferably in a level in which also the rotor cover is situated.

In some embodiments according to the present invention the pre-determined width of the gap is any width smaller than a diameter of a tube used with the pump or designated for use. The diameter may be the one of the tube before use. Alternatively, it can be the diameter of the tube during use, optionally whilst fluid movement devices affect it or whilst they do not affect it.

In some embodiments according to the present invention the width of the gap is smaller than an average or averaged distance between a circular path described by a fluid movement device (e.g. rollers) of the rotor whilst rotating and an average or averaged inner diameter of the stator.

In some embodiments according to the present invention the width of the gap is smaller than the smallest distance between a circular path described by a fluid movement device (e.g. rollers) of the rotor whilst rotating and a maximum inner diameter of the stator.

In some embodiments according to the present invention there is a baseplate to the rotor which lies behind the tube when looking at the pump from the front. In some embodiments according to the present invention in at least one section thereof the baseplate is flattened, cut out or cut off in a way that it allows, makes it simple or simplifies removal of the rotor frontwards out of the stator in the direction of the axis of rotation of the rotor.

In certain embodiments according to the present invention the flattened, cut out or cut off section is designed such that removal of the rotor out of the pump is possible by just moving the rotor along the direction of the axis of rotation of the rotor. This advantageously allows removal without tilting or contorting the rotor. The latter makes the removal advantageously easier and prevents damage that may be caused by the removal.

In some embodiments according to the present invention the area of the stator nearer to the first opening between the separately located openings in a level perpendicular to the axis of rotation in the intended direction of rotation of the rotor is pointed, butted or wedge-formed towards the far end (in relation to the direction of the tube perfusion). This design may additionally prevent or make entangling or injuring at the first opening for insertion of the tube unlikely.

In certain embodiments according to the present invention the blood treatment device is a device for dialysis, in particular hemodialysis, a device for hemofiltration, hemodiafiltration, apheresis, transfusion, oxygenating or similar.

In some embodiments according to the present invention the walling of the stator and/or the walling of the section between the openings with a height or extension (in a direction parallel to the axis of rotation) is designed such that the wall radially surrounds or protects the rotor entirely (with possible exception of the rotor handle). Thus, advantageously almost no place where an entangling or injury could occur remains. This could, if at all, merely happen at the openings for entrance or exit of the tube.

An independent cover of the gap between the rotor and the stator or of the known catching places by mounting a cover produced in an individual work step can in some embodiments according to the present invention be omitted because of the special design of the pump. This advantageously allows keeping costs and expenditure of production and installation low.

Thus, in certain embodiments according to the present invention additional components like a cover for protection from entangling or injury can be dispensed with. This applies especially when the stator and/or the housing of the pump nearer to the axis of rotation, each including the above-mentioned edge, were manufactured by a casting process, e.g. die casting.

The covering, narrowing or constriction, understood as in the before described way, by the area or edge or protrusion having the lesser distance to the axis of rotation ensures or contributes to advantageously avoiding injuries, which could occur in this area when turning the rotor by hand the moment a tubing is inserted in the tubing pump.

BRIEF DESCRIPTION OF THE DRAWINGS

The present invention is described exemplarily by the following drawings in which identical reference numerals describe identical or similar components.

DETAILED DESCRIPTION OF THE DRAWINGS

Figure 1:
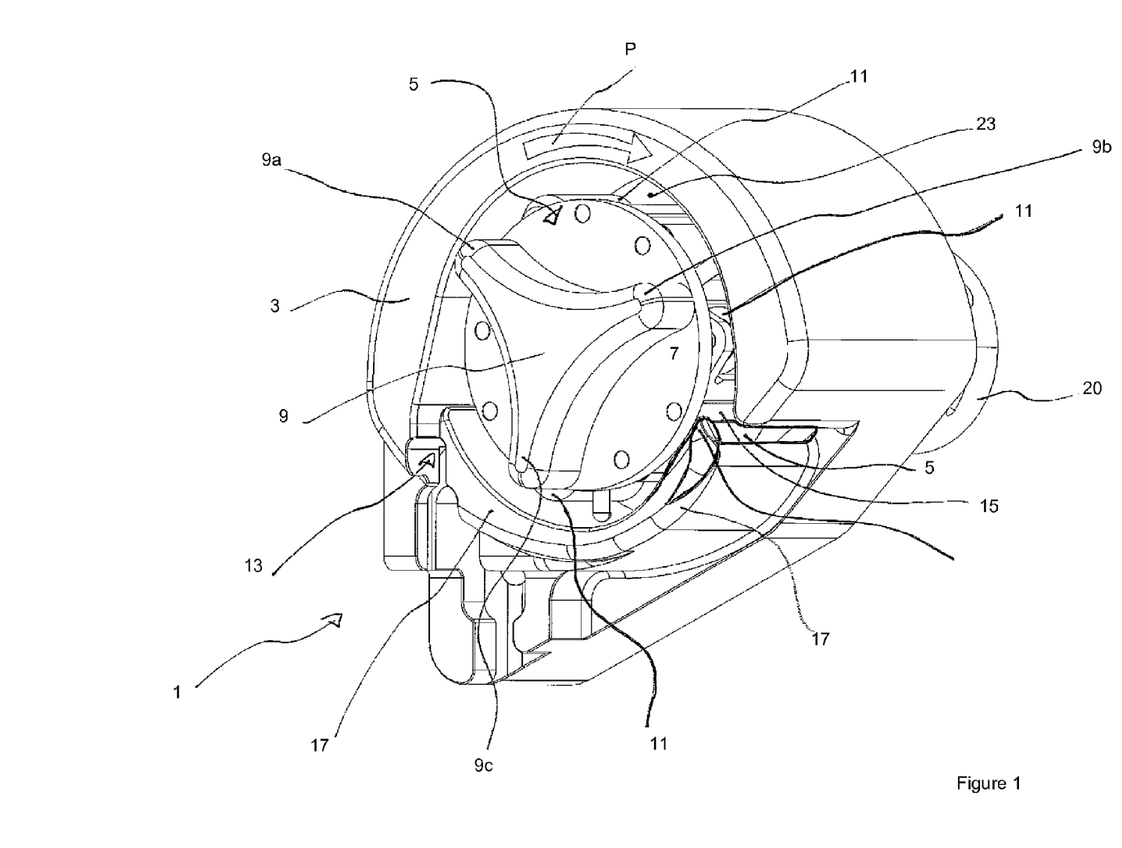
FIG. 1 shows the tubing pump according to the invention in a exemplary embodiment from a front right perspective.

FIG. 1 shows a tubing pump according to the invention or pump 1 in an exemplary embodiment from a front right perspective.

The pump 1 shows a stator 3 which is integrated or produced in one piece with the housing of the pump. Inside the stator 3 a rotor 5 can rotate around an axis of rotation (not shown in FIG. 1). The rotor 5 shows an anterior, rotating cover plate or disc designed as a rotor cover 7. The rotor cover 7 shows an exemplary triple-winged rotor handle 9 with three handle wings 9a, 9b, 9c to manually turn the rotor. The rotor 5 shows rollers 11 as fluid movement devices. In the here described operating state (corresponding standard operation) the rotor 5 rotates into the direction of arrow P.

Between the stator 3 and the rotor 5 a gap visibly remains, into which during use of the pump 1, a section of a tube not shown in the figures is inserted.

When inserting into the gap, which is located between stator 3 and rotor 5, the tube can be led through a first opening 13 into the inner part of the pump 1. After completion of an (estimated) three-quarter circle, the tube eventually can be led out of the inner part of the pump through the second opening 15.

Between the first opening 13 and the second opening 15 is a section 17 which spatially separates both openings 13 and 15.

The section 17 may be part of the stator 3 and/or part of another section of the tubing pump 1. The section 17 shows a thinly designed edge 19—in a direction parallel to the non-marked direction of rotation of the rotor 5—which is nearer to the non-described direction of rotation of the rotor 5 than other sections of the stator 3. This relation, as well as the edge 19 is better shown in FIG. 2.

A drive mechanism unit to power the rotor 5, e.g. arranged as a DC motor or AC motor, is numbered with reference numeral 20.

Figure 2:
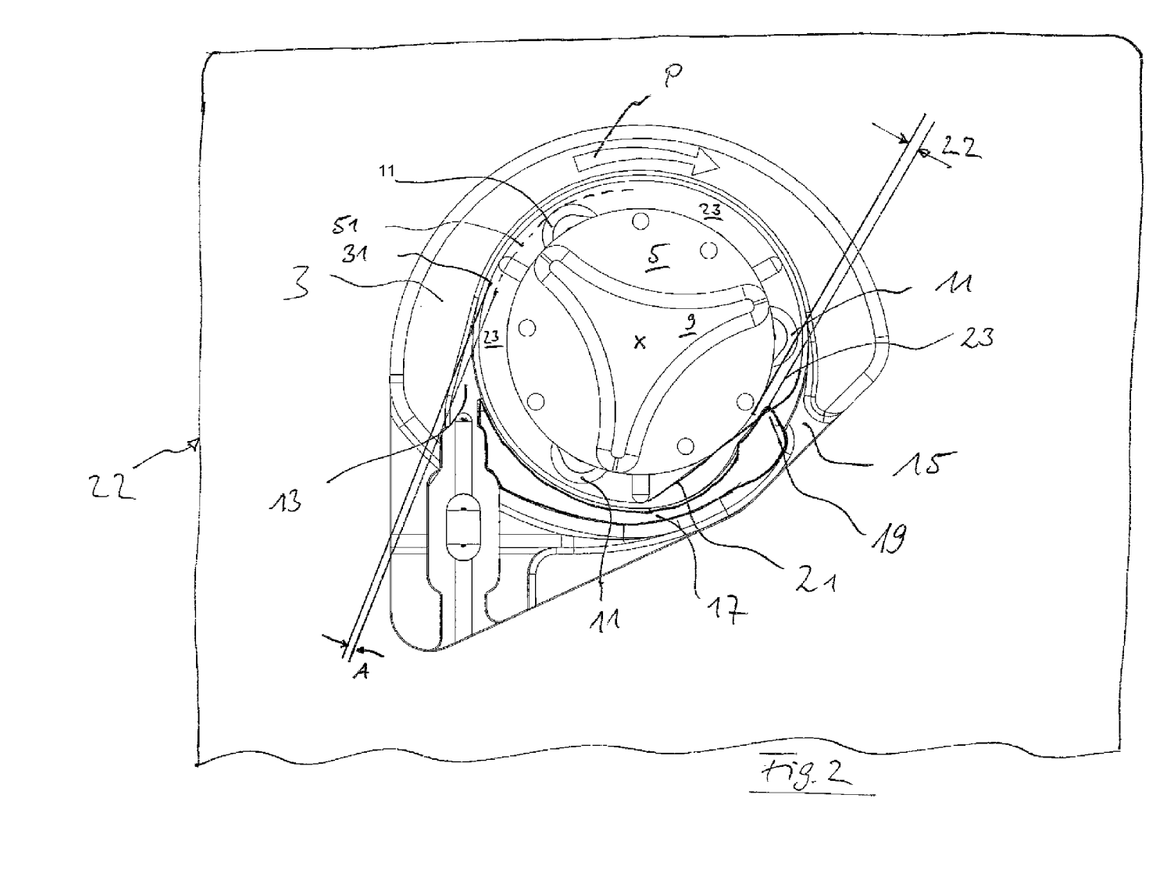
FIG. 2 shows the tubing pump of FIG. 1 from the front.

FIG. 2 shows the tubing pump 1 of FIG. 1 from the front. The edge 19 leads along differently from the remaining course of the section 17. It protrudes nearer to the non-described axis of rotation, which extends through the place marked with x into and out of the depth of the plane of illustration, than some or all other sections of the stator 3.

FIG. 2 shows a gap 22, which lies in a radial direction between the rotating rotor cover 7 and the nearer edge 19. Its width is recognizably smaller than the width of any other distance between the rotor 5 and the stator 3 or section 17 within the plane of illustration (thus in a level perpendicular to the axis of rotation).

In FIG. 2 a flattening 21 of a baseplate 23 of the rotor 5 is visible. The flattening advantageously allows for insertion or removal of the rotor 5 into or out of the stator 3 or into or out of the housing 25 of the pump 1, e.g. for maintenance purposes.

FIG. 2 shows a middle distance A between a circular path 51 (in FIG. 2 indicated as a dotted line) described by the rollers 11 of the rotor 5 during rotation of the rotor 5 and a middle inner diameter 31 of the stator 3 which during standard operation is in contact with the tube.

Furthermore, FIG. 2 indicates highly schematically and only in parts the treatment device according to the present invention.

Figure 3:
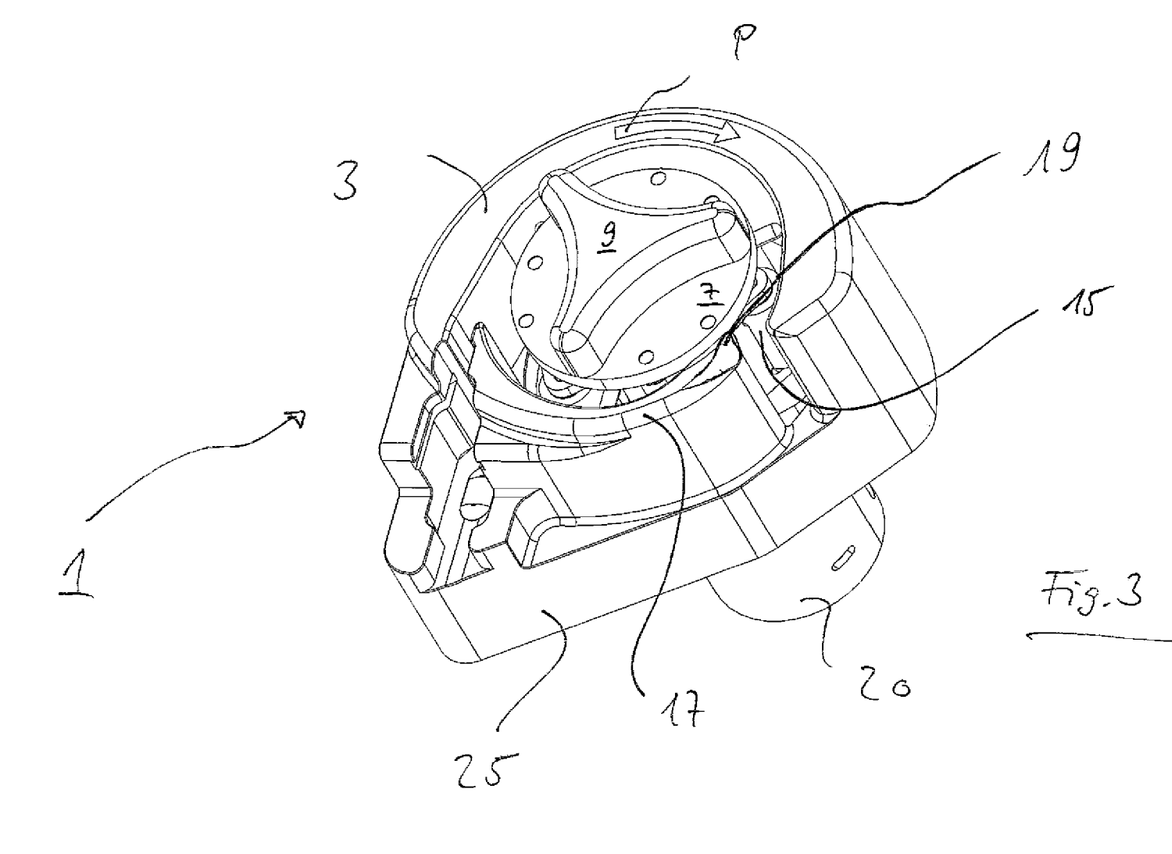
FIG. 3 shows the tubing pump of FIG. 1 from a lower right perspective.

FIG. 3 shows the tubing pump 1 of the previous figures in a perspective from below right.

Figure 4:
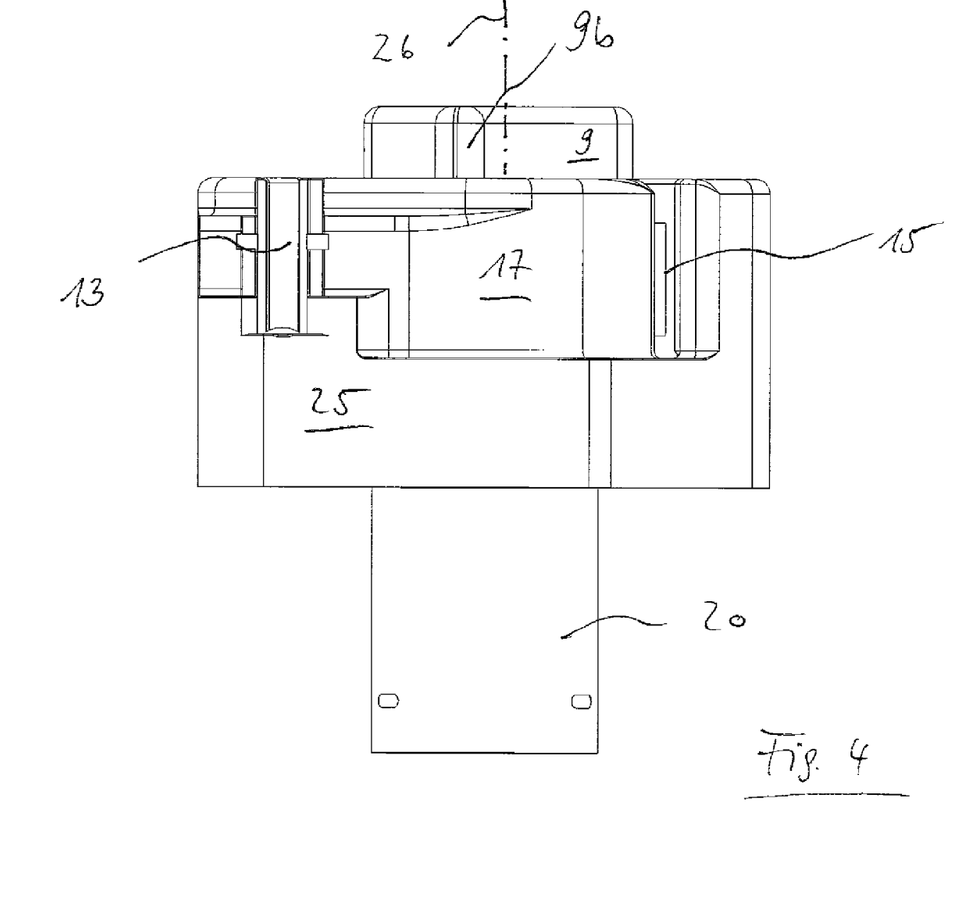
FIG. 4 shows the tubing pump of FIG. 1 from below.

FIG. 4 shows the tubing pump 1 of the previous figures from below.

FIG. 4 clearly shows that the walling of the stator 5, as well as of the section 17, which lies between the openings 13 and 15 is designed upwards in a direction towards the rotor handle 9 such that the walling completely surrounds or protects the rotor 5, with the only exception of the rotor handle.

The axis of rotation of the rotor 5 is marked by reference numeral 26.

Figure 5:
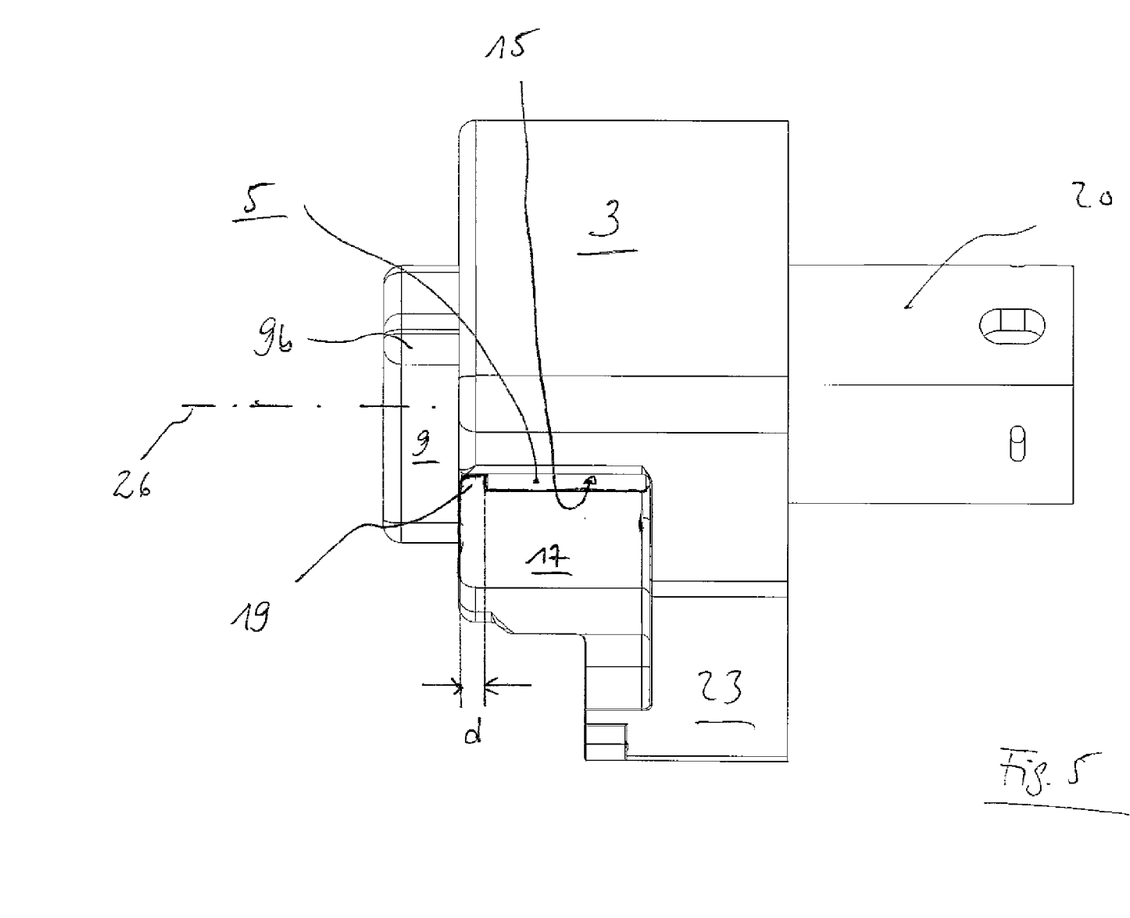
FIG. 5 shows the tubing pump of FIG. 1 from the right.

FIG. 5 shows the tubing pump 1 of the previous figures from the right.

FIG. 5 clearly shows that the edge 19 only slightly extends in a direction d parallel to the axis of rotation. Thus, this edge 19 is designed so thin that in FIG. 5 a view is opened through the second opening 15 onto parts of the rotor 5. A track for the rollers of the rotor 5 which are not shown in FIG. 5 is thus advantageously not affected by the edge 19.

In certain embodiments according to the invention extension d equals the thickness of the rotor cover 7.

Figure 6:
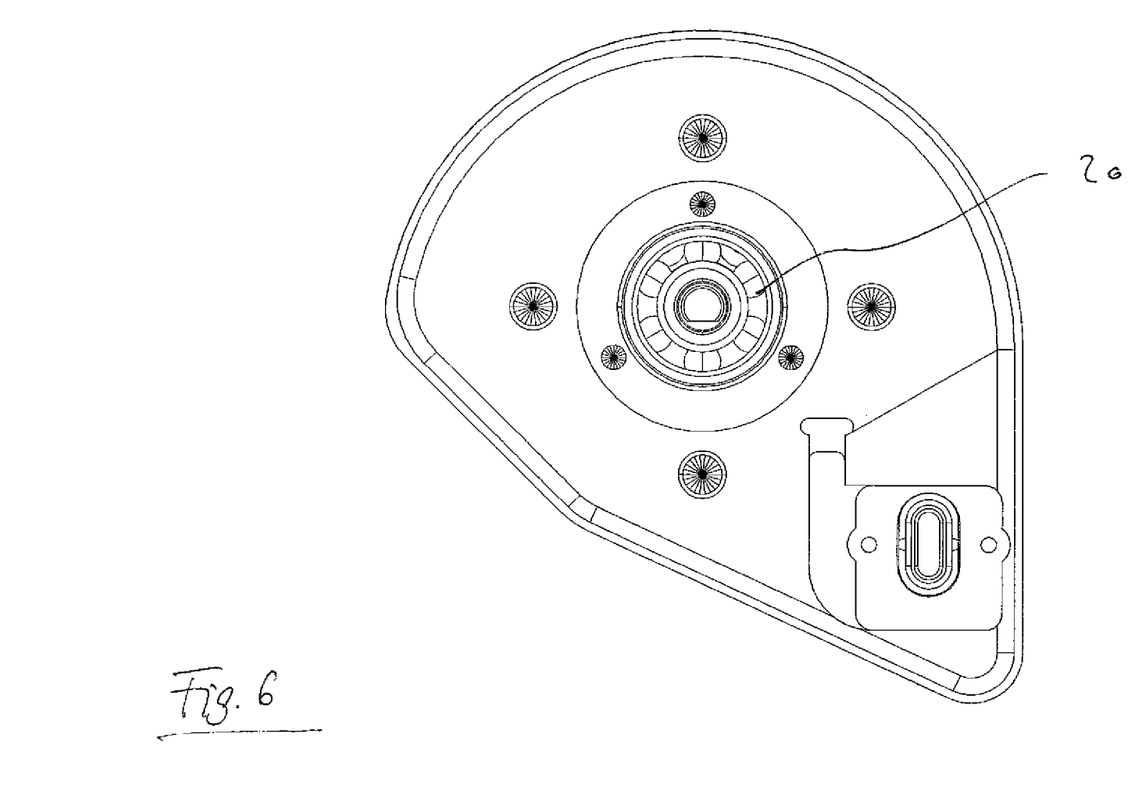
FIG. 6 shows the tubing pump of FIG. 1 from behind.

FIG. 6 shows the tubing pump 1 of the previous figures from behind.

What is claimed is:

1. A flexible tubing pump for accommodation of at least one section of a flexible tubing comprising:
   at least one stator;
   at least one rotor that pivots around an axis of rotation in the stator, wherein the stator surrounds or at least partially confines the rotor;
   a first opening for inserting the flexible tubing into the flexible tubing pump; and
   a separately located second opening for leading the flexible tubing out of the flexible tubing pump, wherein a section of a plurality of sections of the stator or of another part of the flexible tubing pump, or of both, located between the first opening and the second opening has an area or an edge that is nearer to the axis of rotation of the rotor than all other sections of the plurality of sections of the stator located between the first opening and the second opening,
   wherein at least one of the first opening and the second opening opens toward a front of the flexible tubing pump and is visible in a front view of the flexible tubing pump during use of the flexible tubing pump;
   wherein the area or edge which is nearer to the axis of rotation of the rotor is located between the first opening and the second opening and is not in a path of fluid movement or moving devices of the rotor, and
   wherein the area or edge which is nearer to the axis of rotation of the rotor does not redirect the flexible tubing towards a desired direction.

2. The flexible tubing pump according to claim 1, wherein (i) a portion of the stator that surrounds or at least partially confines the rotor, (ii) the section between the first opening and the second opening, or (iii) both, stick out or at least cover the rotor perpendicular to the axis of rotation of the rotor.

3. The flexible tubing pump according to claim 2, wherein the area or edge which is nearer to the axis of rotation of the rotor is narrower towards an end or a tip in a level perpendicular to the axis of rotation, where the tip points against the intended direction of rotation of the rotor.

4. The flexible tubing pump according to claim 2, wherein the rotor comprises:
   a rotor cover that rotates simultaneously with the rotor during use of the flexible tubing pump, and wherein the area or edge which is nearer to the axis of rotation of the rotor is arranged in relation to the flexible tubing pump such that a gap that is between the rotating rotor cover and the area or edge which is nearer to the axis of rotation of the rotor does not exceed a pre-determined width.

5. The flexible tubing pump according to claim 1, wherein the area or edge which is nearer to the axis of rotation of the rotor is narrower towards an end or a tip in a level perpendicular to the axis of rotation, where the tip points against the intended direction of rotation of the rotor.

6. The flexible tubing pump according to claim 1, wherein the rotor comprises:
   a rotor cover that rotates simultaneously with the rotor during use of the flexible tubing pump, and wherein the area or edge which is nearer to the axis of rotation of the rotor is arranged in relation to the flexible tubing pump such that a gap that is between the rotating rotor cover and the area or edge which is nearer to the axis of rotation of the rotor does not exceed a pre-determined width.

7. The flexible tubing pump according to claim 6, wherein the pre-determined width of the gap is smaller than any space between other sections of the stator and the rotor in a level perpendicular to the axis of rotation.

8. The flexible tubing pump according to claim 6, wherein the pre-determined width of the gap is smaller than a diameter of a tube used or adapted to be used with the flexible tubing pump before or during use of the flexible tubing pump.

9. The flexible tubing pump according to claim 6, wherein the pre-determined width of the gap is smaller than a middle distance between a circular path described by movement devices of the rotor during rotation and a middle inner diameter of the stator.

10. The flexible tubing pump according to claim 7, wherein the pre-determined width of the gap is smaller than a middle distance between a circular path described by movement devices of the rotor during rotation and a middle inner diameter of the stator.

11. The flexible tubing pump according to claim 8, wherein the pre-determined width of the gap is smaller than a middle distance between a circular path described by movement devices of the rotor during rotation and a middle inner diameter of the stator.

12. The flexible tubing pump according to claim 1, wherein the rotor has a baseplate having at least one section thereof flattened, cut or cut off to allow removal of the rotor from the stator in the direction of the axis of rotation of the rotor.

13. The flexible tubing pump according to claim 1, wherein the area or segment thereof between the first and second openings in an area at the first opening for inserting of the rotor in a level perpendicular to the axis of rotation is pointed or wedge-formed towards an end in the intended direction of rotation of the rotor.

14. The flexible tubing pump according to claim 1, wherein the area or edge which is nearer to the axis of rotation of the rotor is narrower towards an end or a tip in a level perpendicular to the axis of rotation, where the tip points against the intended direction of rotation of the rotor.

15. The flexible tubing pump according to claim 7, wherein the pre-determined width of the gap is smaller than a diameter of a tube used or adapted to be used with the flexible tubing pump before or during use of the flexible tubing pump.

16. The flexible tubing pump according to claim 1, wherein both of the first opening and the second opening open toward the front of the flexible tubing pump and are visible in the front view of the flexible tubing pump.

17. A blood treatment device comprising at least one tubing pump for accommodation of at least one section of a flexible tubing, said tubing pump comprising:
   at least one stator;
   at least one rotor that pivots around an axis of rotation in the stator, wherein the stator surrounds or at least partially confines the rotor;
   a first opening for inserting the flexible tubing into the at least one tubing pump; and
   a separately located second opening for leading the flexible tubing out of the at least one tubing pump, wherein a section of a plurality of sections of the at least one tubing pump, of the stator, or of both located between the first opening and the second opening has an edge or an area that is nearer to the axis of rotation of the rotor than all other sections of the plurality of sections of the stator located between the first opening and the second opening,
   wherein at least one of the first opening and the second opening opens toward a front of the at least one tubing pump and is visible in a front view of the at least one tubing pump during use of the at least one tubing pump;

wherein the area or edge which is nearer to the axis of rotation of the rotor is located between the first opening and the second opening and is not in a path of fluid movement or moving devices of the rotor, and wherein the area or edge which is nearer to the axis of rotation of the rotor does not redirect the flexible tubing towards a desired direction.

18. A blood treatment device for dialysis comprising at least one tubing pump for accommodation of at least one section of a flexible tubing, said at least one tubing pump comprising:

at least one stator;

at least one rotor that pivots around an axis of rotation in the stator, wherein the stator surrounds or at least partially confines the rotor;

a first opening for inserting the flexible tubing into the at least one tubing pump; and a separately located second opening for leading the flexible tubing out of the at least one tubing pump, wherein a section of a plurality of sections of the at least one tubing pump, of the stator, or of both located between the first opening and the second opening has an edge or an area that is nearer to the axis of rotation of the rotor than all other sections of the plurality of sections of the stator located between the first opening and the second opening, wherein at least one of the first opening and the second opening opens toward a front of the at least one tubing pump and is visible in a front view of the at least one tubing pump during use of the at least one tubing pump;

wherein the area or edge which is nearer to the axis of rotation of the rotor is located between the first opening and the second opening and is not in a path of fluid movement or moving devices of the rotor, and wherein the area or edge which is nearer to the axis of rotation of the rotor does not redirect the flexible tubing towards a desired direction, wherein the blood treatment device is selected from the group consisting of: a hemodialyzer, a hemofiltration device, a hemodiafiltration device, an apheresis device, a transfusion device, or an oxygenating device.

* * * * *